(12) United States Patent
Lastow et al.

(10) Patent No.: US 8,479,729 B2
(45) Date of Patent: *Jul. 9, 2013

(54) DEVICE AND METHOD FOR DEAGGREGATING POWDER

(75) Inventors: Orest Lastow, Lund (SE); Johan Remmelgas, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 299 days.

This patent is subject to a terminal disclaimer.

(21) Appl. No.: 12/809,157

(22) PCT Filed: Dec. 18, 2008

(86) PCT No.: PCT/SE2008/051488
§ 371 (c)(1),
(2), (4) Date: Sep. 24, 2010

(87) PCT Pub. No.: WO2009/082341
PCT Pub. Date: Jul. 2, 2009

(65) Prior Publication Data
US 2011/0226243 A1    Sep. 22, 2011

Related U.S. Application Data

(60) Provisional application No. 61/015,383, filed on Dec. 20, 2007.

(51) Int. Cl.
*A61M 15/00* (2006.01)
*A61M 16/00* (2006.01)

(52) U.S. Cl.
USPC .............................. 128/203.19; 128/203.15

(58) Field of Classification Search
USPC ............. 128/203.12, 203.15, 203.19, 203.21, 128/203.25, 203.29, 204.14; 206/539, 528, 206/532, 538, 540
See application file for complete search history.

(56) References Cited

U.S. PATENT DOCUMENTS

| | | |
|---|---|---|
| 3,872,970 A | 3/1975 | Edison |
| 3,948,264 A | 4/1976 | Wilke et al. |
| 4,210,140 A | 7/1980 | James et al. |

(Continued)

FOREIGN PATENT DOCUMENTS

| | | |
|---|---|---|
| AU | 651910 B | 3/1993 |
| DE | 102005046645 B3 | 7/2006 |

(Continued)

OTHER PUBLICATIONS

International Search Report from PCT Application No. PCT/SE2008/051488 mailed on Mar. 10, 2009.

(Continued)

*Primary Examiner* — Kristen Matter
(74) *Attorney, Agent, or Firm* — Finnegan, Henderson, Farabow, Garrett & Dunner, LLP

(57) ABSTRACT

A device for inhalation of at least one air stream carrying a dose of medicament powder is provided. The device includes a flow passage passing a powder-containing cavity. A part of said flow passage propagates along a generally flat surface region. The flat surface region includes a cavity opening into said powder-containing cavity. The passing of an air stream along said flat surface region and outside said cavity generates an eddy in the cavity and the generated eddy contributes to deaggregation of the powder in said cavity and emptying of the powder from said cavity. Furthermore, a shear driven cavity principle is used in conjunction with such a device and a method of releasing medicament powder.

21 Claims, 3 Drawing Sheets

U.S. PATENT DOCUMENTS

| | | | |
|---|---|---|---|
| 4,446,862 A | 5/1984 | Baum et al. |
| 4,849,606 A | 7/1989 | Martens, III et al. |
| 4,860,740 A | 8/1989 | Kirk et al. |
| 4,946,038 A | 8/1990 | Eaton |
| 5,042,472 A | 8/1991 | Bunin |
| 5,383,850 A | 1/1995 | Schwab et al. |
| 5,469,843 A | 11/1995 | Hodson |
| 5,660,169 A | 8/1997 | Källstrand et al. |
| 5,694,920 A | 12/1997 | Abrams et al. |
| 6,006,747 A | 12/1999 | Eisele et al. |
| 6,234,169 B1 | 5/2001 | Bulbrook et al. |
| 6,637,431 B2 | 10/2003 | Ekelius et al. |
| 6,655,381 B2 | 12/2003 | Keane et al. |
| 6,840,239 B2 | 1/2005 | Myrman |
| 6,871,647 B2 | 3/2005 | Allan et al. |
| 6,948,494 B1 | 9/2005 | Snow |
| 7,395,821 B2 | 7/2008 | Lulla et al. |
| 7,810,495 B2 | 10/2010 | Gumaste |
| 2003/0015195 A1 | 1/2003 | Haaije de Boer et al. |
| 2003/0192539 A1 | 10/2003 | Myrman |
| 2004/0069303 A1 | 4/2004 | Brown et al. |
| 2004/0107963 A1 | 6/2004 | Finlay et al. |
| 2004/0123864 A1 | 7/2004 | Hickey et al. |
| 2006/0237010 A1 | 10/2006 | De Boer et al. |
| 2007/0131576 A1 | 6/2007 | Ehling et al. |
| 2007/0151562 A1 | 7/2007 | Jones et al. |
| 2007/0181123 A1 | 8/2007 | Houzego |
| 2008/0001008 A1 | 1/2008 | Thoemmes et al. |
| 2008/0127974 A1 | 6/2008 | Lastow |
| 2008/0142006 A1 | 6/2008 | Bulbrook |
| 2008/0314384 A1 | 12/2008 | Harris et al. |
| 2009/0084379 A1 | 4/2009 | Goeckner et al. |
| 2009/0114220 A1 | 5/2009 | Wachtel et al. |
| 2010/0000529 A1 | 1/2010 | Prime et al. |
| 2010/0051027 A1 | 3/2010 | Remmelgas et al. |
| 2010/0300442 A1 | 12/2010 | Houzego et al. |
| 2011/0036348 A1 | 2/2011 | Lastow et al. |
| 2011/0083667 A1 | 4/2011 | Briant et al. |

FOREIGN PATENT DOCUMENTS

| | | |
|---|---|---|
| EP | 1 173 368 B1 | 6/2005 |
| EP | 1 844 806 A1 | 10/2007 |
| EP | 1 318 849 B1 | 4/2009 |
| EP | 1 769 818 B1 | 11/2009 |
| GB | 1 472 650 | 5/1977 |
| GB | 1 502 150 | 2/1978 |
| GB | 1 520 062 | 8/1978 |
| GB | 1 521 000 | 8/1978 |
| GB | 2 264 237 A | 8/1993 |
| GB | 2 401 548 A | 11/2004 |
| WO | WO 92/04069 A1 | 3/1992 |
| WO | WO 97/25086 A2 | 7/1997 |
| WO | WO 99/36116 A1 | 7/1999 |
| WO | WO 00/53248 A1 | 9/2000 |
| WO | WO 00/64779 A1 | 11/2000 |
| WO | WO 03/103563 A2 | 12/2003 |
| WO | WO 2005/030305 A1 | 4/2005 |
| WO | WO 2005/081977 A2 | 9/2005 |
| WO | WO 2006/118527 A1 | 11/2006 |
| WO | WO 2007/144614 A1 | 12/2007 |
| WO | WO 2008/008021 A1 | 1/2008 |
| WO | WO 2008/110809 A2 | 9/2008 |
| WO | WO 2009/008832 A1 | 1/2009 |
| WO | WO 2009/152477 A2 | 12/2009 |
| WO | WO 2011/002406 A1 | 1/2011 |

OTHER PUBLICATIONS

Atvars, K. et al., "Experimental and Computational Investigation of an 'Open' Transonic Cavity Flow" *Proceedings of the Institution of Mechanical Engineers, Part G: Journal of Aerospace Engineering* 223(4):357-368 (Apr. 1, 2009).

International Search Report and Written Opinion issued in International Patent Application No. PCT/SE2008/051490; Date of Mailing: Mar. 11, 2009.

Ukeiley, L. et al., "Velocity and surface pressure measurements in an open cavity" *Experiments in Fluids* 38:656-671 (2005).

Zhang, X., "Compressible Cavity Flow Oscillation due to Shear Layer Instabilities and Pressure Feedback" *AIAA Journal* 33(8):1404-1411 (Aug. 1995).

U.S. Appl. No. 12/940,683, filed Nov. 5, 2010 by Lastow et al.: Office Action, dated May 26, 2011.

U.S. Appl. No. 12/940,683, filed Nov. 5, 2010 by Lastow et al.: Office Action, dated Jul. 15, 2011.

U.S. Appl. No. 12/940,683, filed Nov. 5, 2010 by Lastow et al.: Notice of Allowance, dated Dec. 9, 2011.

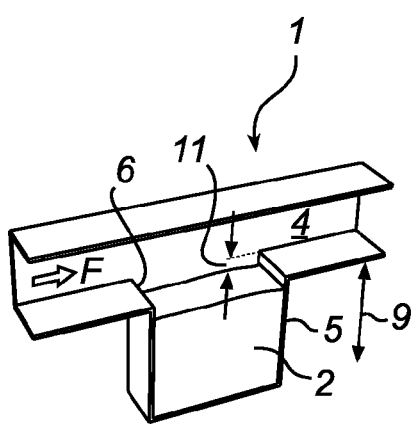
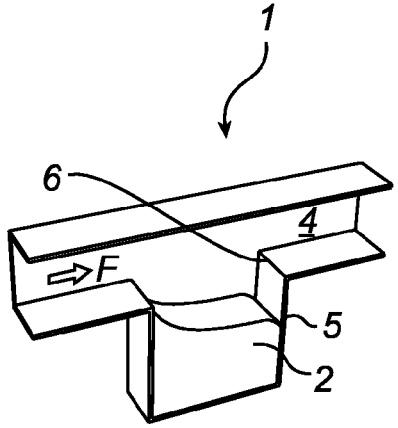
Fig. 3a    Fig. 3b
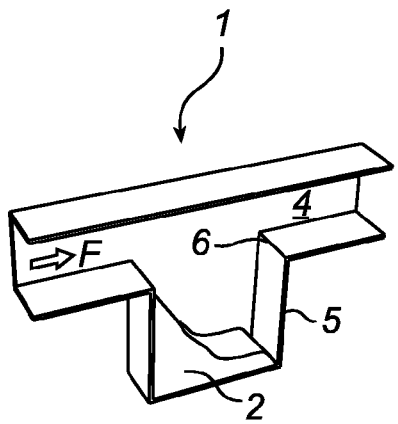
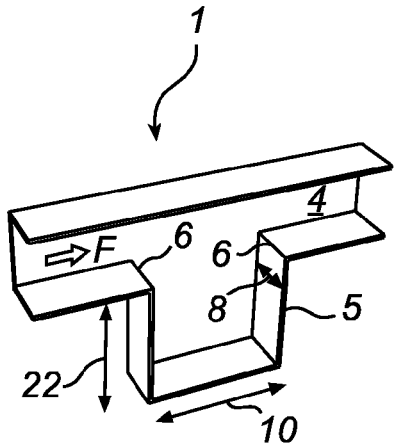
Fig. 3c    Fig. 3d
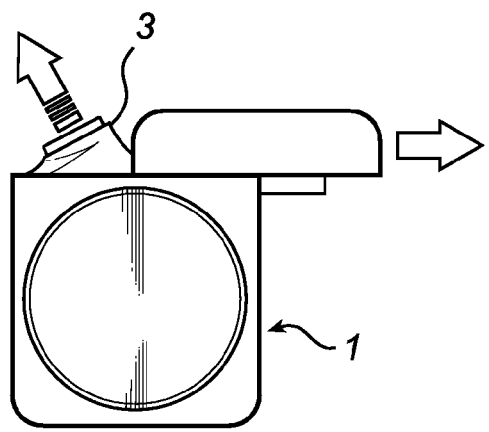
Fig. 4

DEVICE AND METHOD FOR DEAGGREGATING POWDER

This is a U.S. National Phase Application of PCT/SE2008/051488, filed Dec. 18, 2008, which claims the benefit of priority to U.S. Provisional Application No. 61/015,383, filed Dec. 20, 2007, both of which are incorporated herein by reference in their entireties.

FIELD OF THE INVENTION

The invention relates to a device for enabling deaggregation during dispensing of at least one air stream carrying a dose of medicament powder, the device comprising a flow passage passing a powder-containing cavity. Furthermore, the invention relates to a method of deaggregating medicament powder.

BACKGROUND OF THE INVENTION

There are many devices for administering powdered medicaments to the lungs, which employ propellants, such as compressed gases, e.g. air, or liquefied gas propellants, to dispense and disperse the medicament.

There are also a number of known breath actuated inhalation devices for administering powdered medicaments to the lungs, which have mouthpieces through which the medicament is inhaled. British Patent Specification Nos. 1 521 000, 1 520 062, 1 472 650 and 1 502 150 disclose more complex devices in which a complete capsule is inserted into the device thus ensuring no spillage of medicament prior to inhalation, and access to the medicament is gained by piercing the capsule or cutting it in half, inside the dispensing device. On inhalation the air flows into or through the capsule and the powder within is released into the air stream and flows towards the mouth.

U.S. Pat. No. 4,210,140 discloses a device in which access to the powdered medicament is gained by pulling the halves of the capsule apart so that the medicament is emptied to a suitable position for entrainment in the airflow caused by inhalation.

U.S. Pat. No. 6,655,381B2 relates to a pre-metered dose assembly for consistently supplying precise doses of medicament for a breath-actuated dry powder inhaler. The assembly includes a cap defining a dry powder delivery passageway for providing air to a dry powder supply port of a swirl chamber of a breath-actuated dry powder inhaler, and a magazine including a plurality of reservoirs for holding pre-metered doses of dry powder. One of the magazine and the cap is movable with respect to the other of the magazine and the cap for sequentially positioning the reservoirs within the delivery passageway of the cap. A breath-induced low pressure at an outlet port of the inhaler causes an air flow through the dry powder delivery passageway of the assembly and into the dry powder supply port that entrains dry powder from the reservoir positioned in the passageway for inhalation by a patient using the inhaler. The passageway is provided with a venturi in the passageway by the reservoir to create a flow through the reservoir and bring the powder there from.

In spite of the numerous prior art devices there is a need for a device, which is simple to operate, and efficient in administering powdered medicaments into the alveolar region of the lungs. Hence, it is a further object of the present invention to enable the medicament powder to be deaggregated before being administered by the device. In addition to the above mentioned methods of enabling deaggregation in the prior art, there exist various ways of enabling deaggregation by vibrating, shaking or providing alternative obstacles in the flow passage etc. It is common to strive for a deaggregation that makes a significant amount of the powder particles to be in accordance with a desired size and weight. This is often referred to as a classifying of the powder particles. These prior art deaggregation devices may result in contamination of the downstream flow passage since medicament powder may accumulate in the downstream region of the device e.g. by certain alternative obstacles. It is of course desirable to reduce or avoid the risk of administering an inaccurate amount of medicament powder.

SUMMARY OF THE INVENTION

The above-mentioned object is achieved by providing a device of the kind defined herein, characterized in that a part of said flow passage propagates along a flat surface region, said flat surface region comprising an opening into said powder-containing cavity and that the passing of an air stream along said flat surface region and outside said cavity generates an eddy in the cavity and the generated eddy contributes to deaggregation of the powder in said cavity and emptying of the powder from said cavity. The flow passage is arranged to enable guiding of the air stream passing the opening of the cavity on the outside of the cavity opening thereof.

It is found that the build up of an eddy in the cavity will allow for deaggregation. Advantageously, the device is an inhaler. It may be suitable for single as well as multidose type inhalers.

Advantageously, the cavity is brick-shaped and the cavity opening has a rim where the sides of the cavity transcend (change) into the flow passage flat surface region. Thus, the flat surface region may continue both upstream and downstream of the cavity opening. Accordingly, the air stream, when passing the cavity in the flow passage, may flow in parallel with a plane coinciding with the rim of the cavity opening in the flow passage. This is what creates a shear driven cavity flow in the device. More in detail, the flow passage is arranged so that the flow is directed in parallel with the plane coinciding with the rim of the cavity opening in the flow passage where the cavity is located. The sides of the cavity may transcend perpendicularly in the flat surface region.

Since the eddy is developing efficiently when it describes a cylindrical movement pattern it is advantageous that the cavity/cavities in question is/are shaped to allow a cylindrical wind flow pattern within the cavity. It is acknowledged that a cavity is a space in a structure with one opening to the surrounding environment. More in particular, the cavity may have a length in the flow direction (F) of the flow passage which is in the range of 65% to 135% of the cavity depth, such as in the range of 85% to 115% of the cavity depth, for instance in the range of 95% to 105% of the cavity depth. Hence, suitably, the cavity depth does not exceed the value of the length in the flow direction in terms of dimension.

Suitably, at least one cavity side, when taken in a cross section of the cavity as seen from above when the device is in the normal use condition and the opening of the cavity is facing upwards, has a width of the cavity which is in the range of 35% to 135% of the length, of the cavity, as seen in the propagating direction of the flow passage, such as in the range of 45% to 115% of the length of the cavity, for instance in the range of 50% to 100% of the length of the cavity. Consequently, a suitable shape of the cavity cross sectional shape as seen from above is a rectangular shape.

Moreover, the cavity depth and cavity length relation may be such that they form a substantially quadratic cross section.

Hence, the inner corners of the cavity are essentially sharp. The edges of the cavity that propagates transverse to the air stream direction and are present in the bottom of the cavity may have a slightly curved shape in order to provide some guidance in the rotational movement of the generated eddy.

The cavity is provided with a headspace between powder top and the cavity rim; the headspace is at least 1 mm. The distance from the top of the cavity to the top of the particle bed in an initial condition may be 1 mm or more than 1 mm. This distance is referred to as the headspace of the cavity. A headspace of e.g. 3 mm is sufficient for the conditions in the present device but depends also on the total cavity depth. Possibly, the headspace may vary in between 10 to 80% of the cavity depth provided that the shape of the cavity is adapted for deaggregation in accordance with the present invention.

It is also found that the mass flow rate of the device is fairly insensitive to the depth of the cavity. The extent of the headspace may be between 15% and 35% of the cavity depth and the cavity depth, from rim to bottom of a brick-shaped cavity, is between 4 and 10 mm, such as about 5 mm.

It is realized that the design of the present device provides for use of a phenomenon denoted as shear driven cavity principle during deaggregation of the powder in the cavity and emptying operation of the powder there from. Suitably, the flow passage is arranged to follow a generally horizontal line from an inlet port chamber to a mouthpiece when the device is positioned for normal operation.

The shear driven cavity is a model for flow in a cavity where the upper boundary moves in a desired flow direction, and thus causes a rotation in the cavity. The flow occurs at a Reynolds number which is likely higher than 4000 so the upper boundary flow may be assumed to be turbulent in general cases. The patterns during this process are quite complex. In order to support the shear driven cavity flow phenomenon by the cavity the opposing side surfaces of the flow passage are arranged with a broadening propagation in relation to one another. The flow passage may be formed with a constant distance between upper and lower flat surface region in the upstream region in relation to the cavity. Furthermore, it is desirable that the flow passage in the downstream region in relation to the cavity is formed with the same distance as the upstream region. The cross sectional shape of the flow passage in the cavity region is also formed in the same manner. The cross sectional shape of the flow passage may be rectangular with dimensions ranging between 2 to 5 mm.

Rectangular cavities are attractive provided they have an appropriate depth. For these cavities, the emptying time and the wall deposition factor is predicted to increase as the depth increases. The deaggregation potential is predicted to decrease as the depth increases beyond 5 mm, but a local maximum is found for depths near 4 mm. The depth is also important for cavities with inclined walls.

The orientation of the cavity with respect to the flow passage is found to have a significant effect on the emptying time and the deaggregation potential. The cavity depth, the cavity fillet radii, and the channel height are predicted to have only a minor impact on the emptying time and the deaggregation potential. An inspection of the flow behavior suggests that deaggregation is promoted by devices for which an inclination angle $\alpha > 0$ because the cavity affects the air stream in such a way that the powder particles that are about to escape from the cavity are more likely to re-enter the cavity. The particles that fail to escape from the cavity instead impact on the downstream wall of the cavity, which causes deaggregation. Obviously, since particles are less likely to escape the cavity for devices with $\alpha > 0$, the emptying time is longer.

Suitably, it is also provided a device wherein a cavity structure holder, for a cavity structure having a plurality of cavities containing respective doses of powder, is arranged thereto. The cavity structure holder forms part of at least one of the side portions of the flow passage. It is anticipated that the shape of the flow passage allows for a simple design which in turn allows for use of less elements leading to facilitate manufacturing process. Advantageously, a plurality of cavities is integrally formed in said cavity structure.

Moreover, it is a further benefit of the present invention to provide a seal component, such as a foil, which is releasably covering said cavity opening in a pre-inhaling condition. Advantageously, the seal component of the cavity opening is releasable upon breath actuation. The discovery of a device and a method for efficient deaggregation within the cavity allows for a simple design of the outlet leading to a significantly reduced risk for medicament powder to get caught in the downstream area. Thus, it is realized that the administration of medicament powder may be performed in a secure manner with respect to e.g. dose amount.

It is also described a method for deaggregating a medicament powder during dispensing of medicament powder. It is thus disclosed a method for deaggregating a medicament powder in an inhalation device. The method of providing of at least one air stream carrying a dose of medicament powder comprises bringing an air stream to flow straight along a part of a flow passage propagating along a flat surface region, said flat surface region comprising an opening into a powder-containing cavity, and passing the air stream outside said cavity to generate an eddy in the cavity, the eddy contributing to the deaggregation of the powder in the cavity and emptying of the powder from said cavity.

Since the eddy is developing efficiently when it describes a cylindrical movement pattern it is advantageous that the cavity/cavities in question is/are shaped to allow a circular or rather cylindrical wind flow pattern within the cavity. The cylindrical flow pattern in the cavity would be developed around an axis located transverse the flow direction and in the middle of the cavity when the device is held in normal operation condition. It is acknowledged that a cavity is a space in a structure with one opening to the surrounding environment. More in particular, the cavity may have a length in the flow direction (F) of the flow passage which is in the range of 65% to 135% of the cavity depth, such as in the range of 85% to 115% of the cavity depth, for instance in the range of 95% to 105% of the cavity depth. Hence, suitably, the cavity depth does not exceed the value of the length in the flow direction in terms of dimension.

It is common in the art of deaggregation to strive after that powder particles are deaggregated to a desired size and possibly mass weight. By using these proportions the deaggregation due to shear driven cavity in the cavity will be performed efficiently. This means that larger particles may not leave the cavity as easy as smaller powder particles. Thus, larger particles will be subject to some additional loops in the cavity and thus increased deaggregation. Once the larger powder particles have been deaggregated to a suitable size they will leave the cavity. It is one of the benefits of the shear driven cavity principles used in this environment that a classifying effect is enabled.

Consequently, it is found that a suitable shape of the cavity, in any cross section as seen from the side, is an essentially quadratic shape. The inner corners of the cavity are advantageously sharp. The edges of the cavity that propagates transverse to the air stream direction and are present in the bottom of the cavity may have a slightly curved shape in order to provide some guidance in the rotational movement of the generated eddy.

Suitably, at least one cavity side, when taken in a cross section of the cavity as seen from above when the device is in the normal use condition and the opening of the cavity is facing upwards, has a width which is in the range of 35% to 135% of the length in the propagating direction of the flow passage cavity for allowing generation of an eddy with the ability to perform deaggregation and emptying of a cavity. For instance, the cavity opening may have a width in the cavity opening in the range of 45% to 115% of the length of the cavity, such as in the range of 50% to 100% of the length of the cavity.

The medicament-containing cavity may contain various drugs and/or bioactive agents. The bioactive agent may be selected from any therapeutic or diagnostic agent. For example it may be from the group of antiallergics, bronchodilators, bronchoconstrictors, pulmonary lung surfactants, analgesics, antibiotics, leukotrine inhibitors or antagonists, anticholinergics, mast cell inhibitors, antihistamines, anti-inflammatory, antineoplastics, anaesthetics, anti-tubercular, imaging agents, cardiovascular agents, enzymes, steroids, genetic material, viral vectors, antisense agents, proteins, peptides and combinations thereof.

Examples of specific drugs which can be incorporated in the medicament containing cavity according to the invention include mometasone, ipratropium bromide, tiotropium and salts thereof, salemeterol, fluticasone propionate, beclomethasone dipropionate, reproterol, clenbuterol, rofleponide and salts, nedocromil, sodium cromoglycate, flunisolide, budesonide, formoterol fumarate dihydrate, Symbicort™ (budesonide and formoterol), terbutaline, terbutaline sulphate, salbutamol base and sulphate, fenoterol, 3-[2-(4-Hydroxy-2-oxo-3H-1,3-benzothiazol-7-yl)ethylamino]-N-[2-[2-(4-methylphenyl)ethoxy]ethyl]propane-sulphonamide, hydrochloride. All of the above compounds can be in free base form or as pharmaceutically acceptable salts as known in the art.

Combinations of drugs may also be employed, for example formoterol/budesonide; formoterol/fluticasone; formoterol/mometasone; salmeterol/fluticasone; formoterol/tiotropium salts; zafirlukast/formoterol, zafirlukast/budesonide; montelukast/formoterol; montelukast/budesonide; loratadine/montelukast and loratadine/zafirlukast.

Further combinations include tiotropium and fluticasone, tiotropium and budesonide, tiotropium and mometasone, mometasone and salmeterol, formoterol and rofleponide, salmeterol and budesonide, salmeterol and rofleponide, and tiotropium and rofleponide.

BRIEF DESCRIPTION OF THE DRAWINGS

The present invention will now be described, for exemplary purposes, in more detail by way of embodiments and with reference to the enclosed drawings, in which.

DETAILED DESCRIPTION OF THE DRAWINGS

At least one example embodiment of the present invention is an inhalation device from which a user may inhale consecutive doses of medicament in the form of dry powder. Such an inhalation device is illustrated in FIG. 4. The device 1 includes a housing and a mouthpiece 3. The mouthpiece 3 may be uncovered by linear movement of the mouthpiece cover. The mouthpiece cover according to a second embodiment is pivotally supported by the housing of the device 1.

Figure 5:
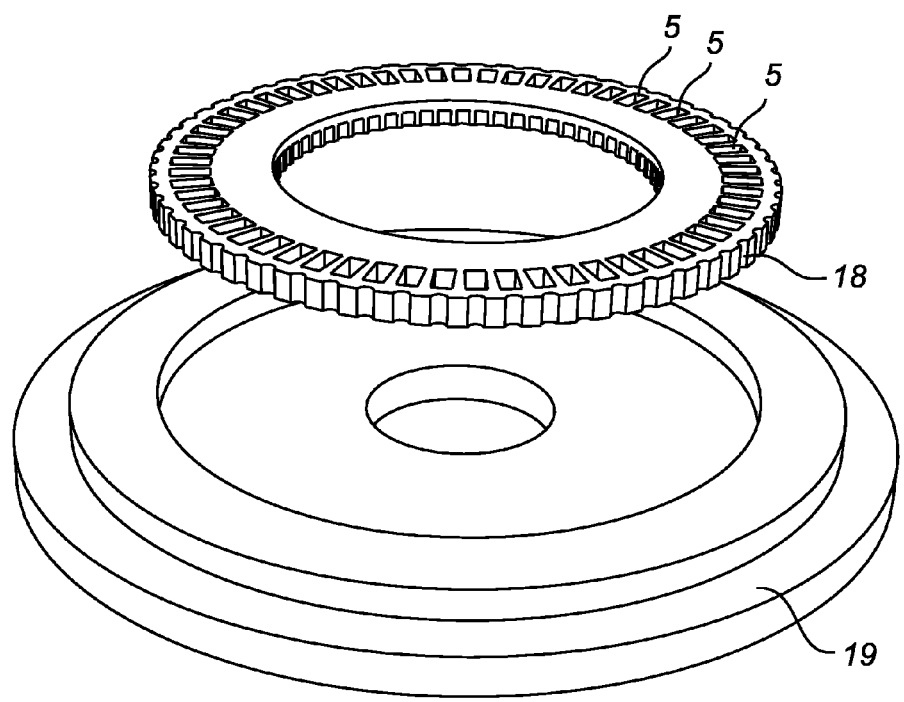
FIG. 5 illustrates an exploded partial view of the inhalation device disclosing the cavity structure holder more in detail.

The device 1 is used for providing medicament powder and part of its interior is disclosed in FIG. 5. Inside the housing there is provided a cavity structure 18 containing a plurality of cavities 5. In accordance with the illustrated embodiment the cavity structure 18 is positioned in a cavity holder 19. The cavity structure 18 may be provided with a plurality of cavities 5 in an annular pattern. Moreover, the cavity structure 18 in accordance with the illustrated embodiment is ring-shaped with a comparatively large hole in the centre thereof. The cavity 5 is brick-shaped and the cavity opening has a rim 6 where the sides of the cavity 5 transcend into the flow passage flat surface 7 region. The eddy is developing efficiently when it describes a circular movement pattern. It is advantageous that the cavity/cavities 5 in question is/are shaped to allow a cylindrical wind flow pattern within the cavity 5. The cylindrical flow pattern in the cavity would be developed around an axis located transverse the flow direction and in the middle of the cavity when the device is held in normal operation condition. The sides of the cavity may transcend perpendicularly in the flat surface region of the cavity structure 18 which in turn is aligned with the flat surface of the cavity holder 19 providing for an appropriate flow direction in the flow passage (not shown in FIG. 5).

Figure 1:
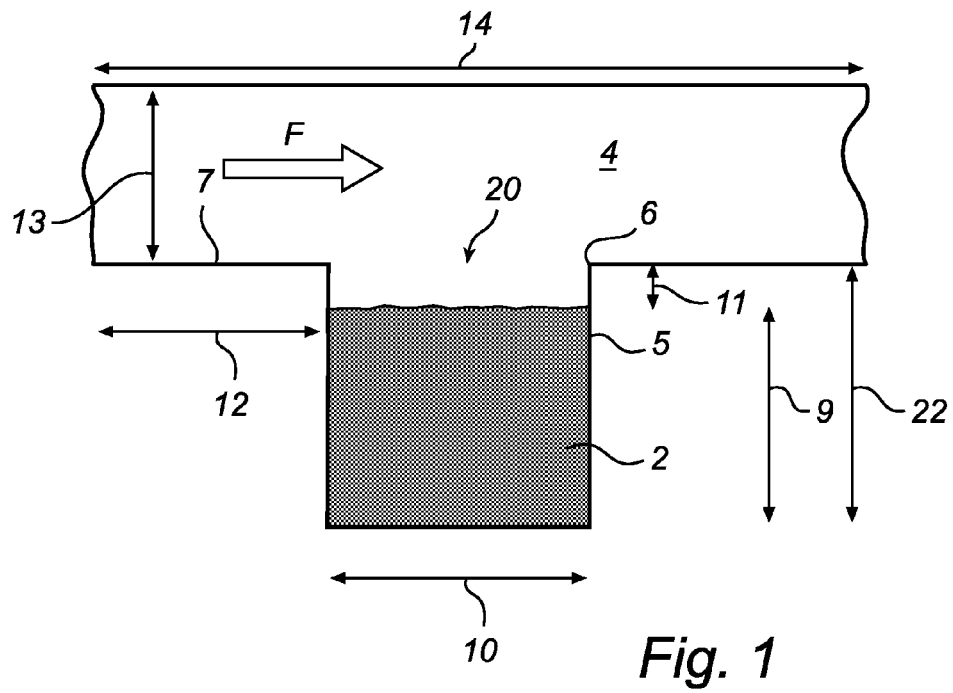
FIG. 1 is a schematic cross sectional view of a flow passage region of at least one example embodiment.

Now, with reference to FIG. 1 the overall function of the device 1 according to a at least one example embodiment of the invention will be described in more detail. Part of the flow passage 4 propagates along a flat surface region 7. The flat surface region 7, which forms the bottom of the flow passage 4 when the device 1 is in its intended use condition, comprises a cavity opening 20 into said powder-containing cavity 5. The passing of an air stream in the flow direction (F) along said flat surface region 7 and outside said cavity 5 generates an eddy in the cavity 5 and the generated eddy contributes to deaggregation of the powder 2 in said cavity 5. The powder particles are brought against the sides within the cavity 5 when the shear driven cavity eddy is generated. When the powder particles hit the sides of the cavity 5 they become deaggregated and thus appropriate for administration. Furthermore, the generated eddy contributes to the emptying of the powder 2 from said cavity 5.

More in particular the cavity 5 and cavity opening 20 each have a length 10 in the flow direction (F) of the flow passage 4 which is in the range of 65% to 135% of said cavity depth 22. More suitable, the cavity 5 and cavity opening 20 each have a length 10 in the flow direction (F) of the flow passage which is in the range of 85% to 115% of the cavity depth 22, such as in the range of 95% to 105% of the cavity depth 22 of said cavity 5. More in detail one cavity side, when taken in a cross section of the cavity as seen from above when the device is in the normal use condition and the opening of the cavity is facing upwards, has a width 8 in the propagating direction of the flow passage 4 which is in the range of 35% to 135% of the length 10 of the cavity 5, such as in the range of 45% to 115% of the length 10 of the cavity 5, for instance in the range of 50% to 100% of the length 10 of the cavity 5.

The distance from the top of the cavity 5 to the top of the powder particle bed in an initial condition may, for instance, be 1 mm or more than 1 mm. This distance is referred to as the headspace 11 of the cavity. The cavity 5 is provided with a headspace 11 between powder top and the cavity rim 6; the headspace 11 is at least 1 mm. A headspace 11 sufficient for the conditions for inhalation devices 1 according to the present invention. A headspace ranging in between 1-3 mm would be sufficient for the conditions in the present inhaler but depends also on the total cavity depth. Possibly, the headspace may vary in between 10 to 80% of the cavity depth provided that the shape of the cavity is adapted for deaggregation in accordance with the present invention. It is also found that the mass flow rate of the device 1 is fairly insensitive to the depth 22 of the cavity, at least following an initial induction period of approximately 5-10 ms. The extent of the headspace 11 may be between 10 and 35% of the cavity depth 22 and the cavity depth 22, from rim 6 to bottom of a brick-shaped cavity 5, is between 4 and 10 mm.

Consequently, a suitable cross sectional shape of the cavity 5, as seen from the side, is a quadratic shape. The inner corners of the cavity are essentially sharp. The edges 16, 17 of the cavity 5 that propagates transverse to the air stream direction and are present in the bottom of the cavity 5 may have a slightly curved shape (not shown in FIG. 1) in order to provide some guidance in the rotational movement of the generated eddy.

Figure 2:
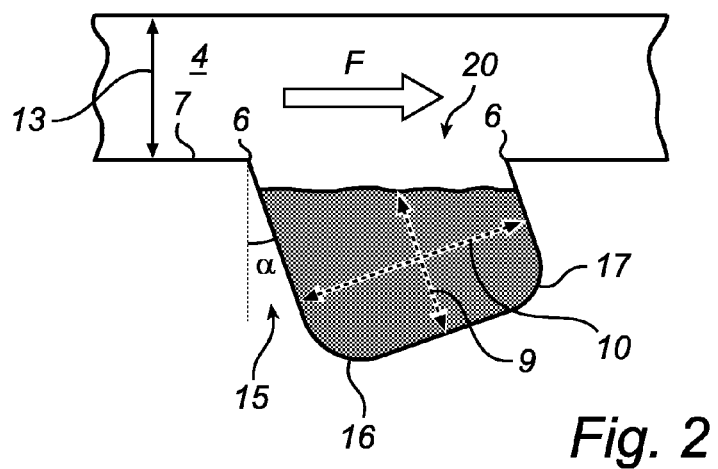
FIG. 2 is a schematic cross sectional view of an alternative flow passage region of an alternative embodiment, FIGS. 3a-3d disclose an inhalation sequence in principle by means of a schematic perspective view in cross section, FIG. 4 discloses a side view of an inhalation device according to at least one example embodiment.

In FIG. 2 a second embodiment of the present invention is disclosed. The sides of the cavity 5 are positioned with an angle ($\alpha$) in relation to a normal direction to the flow direction (F). The rim 6 of the cavity opening 20 will still be aligned with a plane parallel to the flow direction of the air stream in the flow passage region 4 by the cavity 5. The inclination of the side walls in relation to the flow passage 4 will make it more difficult for the generated eddy to provide for dispensing of powder from the cavity 5. Hence, a design in accordance with the second embodiment will increase the time during which the medicament powder 2 is subject to wall contact impact and hence the deaggregation time period may be extended. On the other hand the emptying time will, in analogy with the above explained also be longer for the second embodiment compared to a similar type but with a design in accordance with FIG. 1. It is also found that the flow in the device is qualitatively similar for most flow rates.

Computational studies with brick- and capsule shaped cavities 5 were performed and it was found that a brick shaped cavity 5 showed more promising results than a capsule shaped cavity. The rate of emptying is found to be slightly slower for the device 1 with a capsule shaped cavity. While the flow in the brick shaped cavity 5 is found to be substantially two-dimensional, the flow in the capsule shaped cavity is found to be three-dimensional. The three-dimensional flow in the capsule shaped cavity is found to result in a greater concentration of particles at and near the centerline down stream of the cavity. The major difference, however, is in the capacity of enabling a cylindrical flow pattern leading in turn to an appropriate deaggregation. It is anticipated that the shape of the cylindrical capsule does not allow for a build up of a cylindrical flow pattern.

Now continuing, with reference to FIG. 2 and the shape of the cavity 5. The bottom most edges 16, 17, of a substantially brick shaped cavity, located in the transverse direction in relation to the flow direction (F) may have a curved shape. The first edge 17 in the more downstream position in relation to the second edge 16 has a shorter radius than said second edge 16. The first arrow 9 indicates how the cavity powder depth is measured. The headspace 11 is the distance between the top of the dry powder and the rim 6 of the cavity 5. The length 10 of the cavity is also illustrated in FIG. 2 with an arrow carrying reference number 10.

Continuing to FIGS. 3_a_-3_d_ the dispensing principle in accordance with at least one example embodiment of the invention is further explained. It is realized that the design of the present device 1 provides for use of a phenomenon denoted as shear driven cavity principle during deaggregation of the powder 2 in the cavity 5 and emptying operation of the powder 2 there from. Suitably, the flow passage 4 is arranged to follow a generally horizontal line from an inlet port to a mouthpiece when the device 3 is positioned for normal operation. The flow passage is arranged to guide the air stream passing the opening of the cavity on the outside of the cavity opening thereof.

In FIG. 3_a_ it is disclosed a cavity 5 which is filled with powder 2 with a suitable headspace 11. An air stream along the flow passage 4 is initiated in the flow direction (F) and emptying of the cavity 5 starts. Moving to FIG. 3_b_ in which some of the powder 2 has left the cavity 5. The build up of an eddy air stream in the cavity 5 has begun and it is seen that the cavity 5 is emptied in the downstream region and further upstream when moving to FIG. 3_c_. The time period elapsed from the situation in FIG. 3_a_ to that in FIG. 3_d_ when the emptying of the cavity 5 is completed depends of course on the size and magnitude of flow, depth, powder composition, powder depth, headspace etc. In at least one example embodiment the emptying time including deaggregation is from 30 ms. For instance, the emptying time including deaggregation may be 500 ms.

The shear driven cavity is a model for flow in a cavity 5 where the upper boundary moves in a desired flow direction (F), and thus causes a rotation of gas/air in the cavity 5. The flow occurs at a Reynolds number which is likely higher than 4000 so the upper boundary flow may be assumed to be turbulent in general cases. The patterns during this process are quite complex. The opposing side surfaces of the flow passage 4 are arranged with a broadening propagation in relation to one another in the flow direction. A device comprising a disc in accordance with the embodiment of FIG. 5 which has 60 cavities will have side walls of the flow passage which broadens at an angle of 4 degrees in relation to a centerline of the flow passage.

In an alternative embodiment in which the disc is provided with 30 cavities the side walls of the flow passage broadens at an angle of 12 degrees in relation to a centerline of the flow passage. The flow passage 4 may be formed with a constant distance between upper and lower flat surface region in the upstream region in relation to the cavity 5. Furthermore, it is desirable that the flow passage 4 in the downstream region in relation to the cavity 5 is formed with the same distance as the upstream region. The cross sectional shape of the flow passage 4 in the cavity region is also formed in the same manner. The cross sectional shape of the flow passage 4 may be rectangular with dimensions ranging between 1 to 5 mm.

According to a third embodiment of the invention the device is a single inhalation device containing one cavity with medicament powder.

Rectangular cavities 5 are attractive provided they have an appropriate depth. For these cavities, the emptying time and the wall deposition factor is predicted to increase as the depth increases. The deaggregation potential is predicted to decrease as the depth increases beyond 5 mm, but a local maximum is found for depths near 4 mm. The depth is also important for cavities with inclined walls.

The orientation of the cavity with respect to the flow passage is found to have a significant effect on the emptying time and the deaggregation potential. The cavity depth, the cavity fillet radii, and the channel height are predicted to have only a minor impact on the emptying time and the deaggregation potential. An inspection of the flow behavior suggests that deaggregation is promoted by devices 1 for which α>0 because the cavity 5 affects the air stream in such a way that the powder 2 particles that are about to escape from the cavity are more likely to re-enter the cavity. The particles that fail to escape from the cavity 5 instead impact on the downstream wall of the cavity 5, which causes deaggregation. Since particles are less likely to escape the cavity for devices with α>0, the emptying time is longer.

It is realised that the features of the above presented embodiments is not a complete description of all aspects of the invention and further combinations of features from different embodiments are conceivable within the claimed scope of protection. Hence, it is possible to combine various features with different embodiments within the claimed scope for enabling further aspects of the invention.

The invention claimed is:

1. An inhalation device for enabling deaggregation of a medicament powder during dispensing of the medicament powder, the device comprising:
    a cavity containing the medicament powder; and
    a flow passage including a flat surface region being devoid of a seal component and having an opening into the cavity, wherein an air stream passing along the flat surface region and outside the cavity will generate an eddy in the cavity, such that the generated eddy contributes to deaggregation of the medicament powder in the cavity and emptying of the medicament powder from the cavity,
    wherein the cavity has a substantially straight downstream edge that extends generally transverse to the direction of the air stream on the flat surface region and a substantially straight upstream edge that extends generally transverse to the direction of the air stream on the flat surface region, the flow passage about the cavity is substantially free of any protrusion extending into the flow passage about the cavity, and the flow passage has opposing side surfaces extending along sides of the opening, the entire length of the opposing side surfaces extending along the entire length of sides of the opening being arranged in a diverging relationship in the direction of the air stream.

2. The inhalation device of claim 1, wherein the cavity has a cavity length in a direction of flow of the air stream and a cavity width that is transverse to the direction of the air stream, such that the cavity has a substantially quadratic cross-section defined by the cavity length and the cavity width.

3. The inhalation device of claim 1, wherein the cavity has a cavity length in a direction of flow of the air stream and a cavity width that is transverse to the direction of the air stream, such that the cavity has a substantially rectangular cross-section defined by the cavity length and the cavity width.

4. The inhalation device of claim 1, wherein the cavity is part of a cavity structure having a plurality of cavities containing respective doses of medicament powder, the inhalation device further including:
    a cavity holder for holding the cavity structure, wherein the plurality of cavities are arranged in an annular pattern in the cavity structure.

5. The inhalation device of claim 4, wherein the cavity structure holder forms part of at least one side portion of the flow passage.

6. The inhalation device of claim 1, wherein the flow passage is substantially free of any deaggregation mechanism located downstream of the cavity.

7. An inhalation device for enabling deaggregation of a medicament powder during dispensing of the medicament powder, the device comprising:
    a cavity containing the medicament powder; and
    a flow passage including a flat surface region having an opening into the cavity and a flat top surface located opposite the flat surface region and extending from upstream of the opening to downstream of the opening, wherein the flat top surface is substantially free of any protrusion extending into the flow passage and an air stream passing between the flat top surface and the flat surface region and outside the cavity will generate an eddy in the cavity, such that the generated eddy contributes to deaggregation of the medicament powder in the cavity and emptying of the medicament powder from the cavity;
    wherein the flow passage further includes opposing flat side surfaces extending along sides of the opening, and
    wherein the opposing flat side surfaces, the flat surface region, and the flat top surface form a rectangular cross-section, and the entire lengths of the opposing flat side surfaces extending along the entire length of sides of the opening are arranged in a diverging relationship in the direction of the air stream.

8. The inhalation device of claim 7, wherein the flat surface region upstream of the opening into the cavity is devoid of a seal component.

9. An inhalation device for enabling deaggregation of a medicament powder during dispensing of the medicament powder, the device comprising:
    a cavity containing the medicament powder; and
    a flow passage including a flat surface region having an opening into the cavity, wherein an air stream passing along the flat surface region and outside the cavity will generate an eddy in the cavity, such that the generated eddy contributes to deaggregation of the medicament powder in the cavity and emptying of the medicament powder from the cavity,
    wherein the cavity has a cavity length in a direction of flow of the air stream and a first cavity width along at least one edge of the cavity transverse to the direction of the air stream, such that the cavity has a substantially quadratic cross-section defined by the cavity length and the first cavity width, and the flow passage has opposing side surfaces extending along sides of the opening, the entire length of the opposing side surfaces extending along the entire length of sides of the opening being arranged in a diverging relationship in the direction of the air stream.

10. The inhalation device of claim 9, wherein the cavity has a cavity depth defined by the distance to the bottom of the cavity, wherein the cavity length is in the range of about 65% to about 135% of the cavity depth.

11. The inhalation device of claim 10, wherein the cavity length is in the range of about 115% to about 135% of the cavity depth.

12. The inhalation device of claim 9, wherein the first cavity width is in the range of about 35% to about 45% of the cavity length.

13. The inhalation device of claim 9, wherein the cavity has inner walls defining corners that extend downward from the top of the cavity to the bottom of the cavity, wherein the downward corners define a sharp angle at which two of the inner walls meet.

14. The inhalation device of claim 13, wherein the sharp corner defines a substantially right angle.

15. The inhalation device of claim 14, wherein the cavity has a first bottom edge defined by a downstream wall of the cavity extending generally transverse to the air stream at the bottom of the cavity and a second bottom edge defined by an upstream wall of the cavity extending generally transverse to the air stream at the bottom of the cavity, wherein the first and second bottom edges have a curved shape.

16. The inhalation device of claim 9, wherein the cavity has a headspace defined by the distance between the top of the cavity and the top of the medicament powder in an initial condition, the headspace being at least about 1 mm.

17. The inhalation device of claim 9, the cavity further including:

a downstream wall extending generally transverse to the air stream, wherein the downstream wall is positioned at an inclination angle relative to the direction of flow of the air stream, wherein the angle is greater than zero degrees.

18. The inhalation device of claim 9, wherein the opposing side surfaces are flat.

19. The inhalation device of claim 9, wherein the opposing side surfaces extending along sides of the opening, the flat surface region, and a top surface located opposite the flat surface region form a rectangular cross-section.

20. An inhalation device for enabling deaggregation of a medicament powder during dispensing of the medicament powder, the device comprising:

a cavity containing the medicament powder; and a flow passage including a flat surface region having an opening into the cavity, wherein an air stream passing over the flat surface region will generate an eddy in the cavity to contribute to deaggregation of the medicament powder in the cavity, wherein the cavity has a substantially straight downstream edge that extends generally transverse to the direction of the air stream on the flat surface region and a substantially straight upstream edge that extends generally transverse to the direction of the air stream on the flat surface region, and the flow passage about the cavity is substantially free of any protrusion extending into the flow passage; and wherein the flow passage has opposing side surfaces extending along sides of the opening, the entire length of the opposing side surfaces extending along the entire length of sides of the opening being arranged in a diverging relationship in the direction of the air stream.

21. The inhalation device of claim 20, wherein the opposing side surfaces extending along sides of the opening, the flat surface region, and a top surface located opposite the flat surface region form a rectangular cross-section.

* * * * *